United States Patent [19]

Lippincott, III et al.

[11] Patent Number: 5,405,401
[45] Date of Patent: Apr. 11, 1995

[54] PROSTHESIS FOR REPLACEMENT OF JOINTS BETWEEN LONG BONES IN THE HAND

[75] Inventors: Albert L. Lippincott, III, Prior Lake; Ronald L. Linscheid; William P. Cooney, III, both of Rochester, all of Minn.

[73] Assignees: Orthomet, Inc., Minneapolis; Mayo Foundation, Rochester, both of Minn.

[21] Appl. No.: 132,300

[22] Filed: Oct. 5, 1993

[51] Int. Cl.⁶ .................................................. A61F 2/42
[52] U.S. Cl. ........................................ 623/21; 623/18
[58] Field of Search .............................. 623/18, 20, 21

[56] References Cited

U.S. PATENT DOCUMENTS

| | | |
|---|---|---|
| 3,462,765 | 8/1969 | Swanson . |
| 3,466,669 | 9/1969 | Flatt . |
| 3,506,982 | 4/1970 | Steffee . |
| 3,593,342 | 7/1971 | Niebauer et al. . |
| 3,638,243 | 2/1972 | Campbell, Jr. et al. . |
| 3,651,521 | 3/1972 | Devas . |
| 3,739,403 | 6/1973 | Nicolle . |
| 3,760,427 | 9/1973 | Schultz . |
| 3,772,709 | 11/1973 | Swanson . |
| 3,805,302 | 4/1974 | Mathys . |
| 3,818,513 | 6/1974 | Pillet . |
| 3,824,631 | 7/1974 | Burstein et al. . |
| 3,875,594 | 4/1975 | Swanson . |
| 3,886,600 | 6/1975 | Kahn et al. . |
| 3,946,445 | 3/1976 | Bentley et al. . |
| 3,986,212 | 10/1976 | Sauer . |
| 3,990,116 | 11/1976 | Fixel et al. . |
| 3,990,118 | 11/1976 | Strickland et al. . |
| 3,991,425 | 11/1976 | Martin et al. . |
| 3,992,726 | 11/1976 | Freeman et al. . |
| 4,011,603 | 3/1977 | Steffee . |
| 4,059,854 | 11/1977 | Laure . |
| 4,064,568 | 12/1977 | Grundei et al. .................. 623/20 |
| 4,106,128 | 8/1978 | Greenwald et al. . |
| 4,158,893 | 6/1926 | Swanson . |
| 4,194,250 | 3/1980 | Walker . |
| 4,204,284 | 5/1980 | Koeneman . |
| 4,213,208 | 7/1980 | Marne . |
| 4,231,121 | 11/1980 | Lewis . |

(List continued on next page.)

FOREIGN PATENT DOCUMENTS

| | | | |
|---|---|---|---|
| 49298 | 4/1982 | European Pat. Off. ............. | 623/18 |
| 572339 | 12/1993 | European Pat. Off. ............. | 623/21 |
| 2605878 | 5/1988 | France ................................ | 623/21 |
| 1333412 | 10/1973 | United Kingdom ................ | 623/18 |
| 9300053 | 1/1993 | WIPO . | |

*Primary Examiner*—David Isabella
*Assistant Examiner*—Laura Fossum
*Attorney, Agent, or Firm*—Fredrikson & Byron

[57] ABSTRACT

A joint prosthesis for replacing a joint between two elongated bones of the hand. A first member is provided with an elongated stem for reception in one of the elongated bones and includes a head remote from the stem, the head having a convex articulating surface and lateral articulating surfaces adjacent the convex surface and on each side thereof. A second member has a stem for reception in the other bone and a base remote from the stem, the base having a concave articulating surface and lateral articulating surfaces on each side thereof, the concave and lateral surfaces being adapted to engage and articulate with the respective convex and lateral articulating surfaces of the first member. The lateral articulating surfaces of the first and second members being positioned to fully engage and articulate with each other to thereby restrain lateral articulation only when the bones are articulated through at least 30 degrees of flexion, and at 90 degrees of flexion, the force between said members is borne primarily by said lateral articulating surfaces.

14 Claims, 6 Drawing Sheets

U.S. PATENT DOCUMENTS

| | | | |
|---|---|---|---|
| 4,242,759 | 1/1981 | White . | |
| 4,246,662 | 1/1981 | Pastrick . | |
| 4,301,552 | 11/1981 | London | 623/18 |
| 4,304,011 | 12/1981 | Whelan, III . | |
| 4,313,232 | 2/1982 | Habal et al. . | |
| 4,352,212 | 10/1982 | Greene et al. . | |
| 4,367,562 | 1/1983 | Gauthier . | |
| 4,375,703 | 3/1983 | Evans et al. . | |
| 4,516,569 | 5/1985 | Evans et al. . | |
| 4,634,444 | 1/1987 | Noiles | 623/20 |
| 4,634,445 | 1/1987 | Helal . | |
| 4,685,919 | 8/1987 | Niwa . | |
| 4,759,768 | 7/1988 | Hermann et al. . | |
| 4,911,719 | 3/1990 | Merle . | |
| 4,944,758 | 7/1990 | Bekki et al. . | |
| 4,955,916 | 9/1990 | Carignan et al. . | |
| 4,959,071 | 9/1990 | Brown et al. | 623/20 |
| 5,007,932 | 4/1991 | Bekki et al. . | |
| 5,047,059 | 9/1991 | Saffar . | |
| 5,092,896 | 2/1992 | Meuli et al. . | |
| 5,133,761 | 7/1992 | Krouskop . | |
| 5,219,362 | 6/1993 | Tuke et al. | 623/20 |
| 5,246,460 | 9/1993 | Goodfellow et al. | 623/20 |
| 5,314,479 | 5/1994 | Rockwood, Jr. et al. | 623/19 |

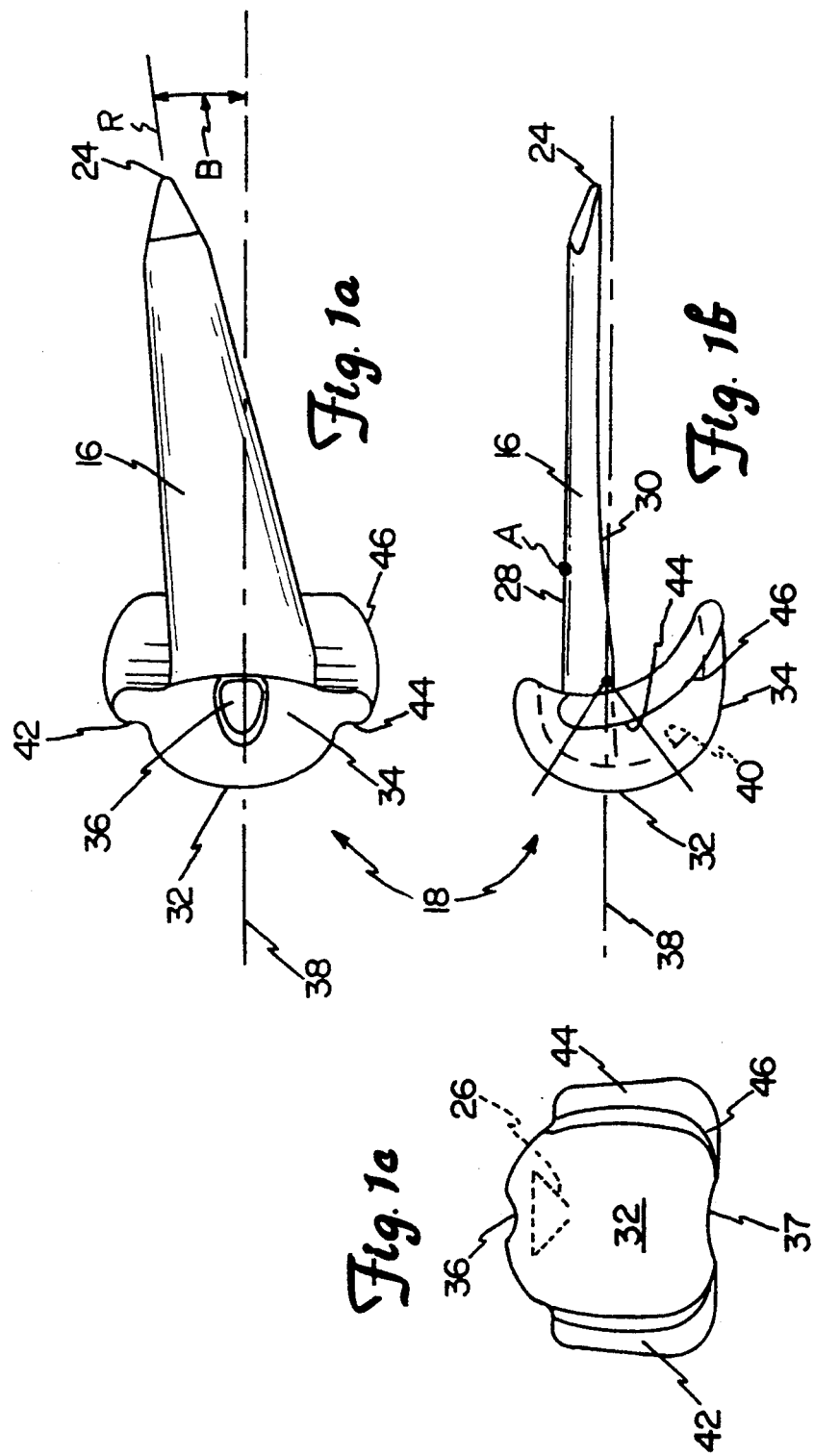

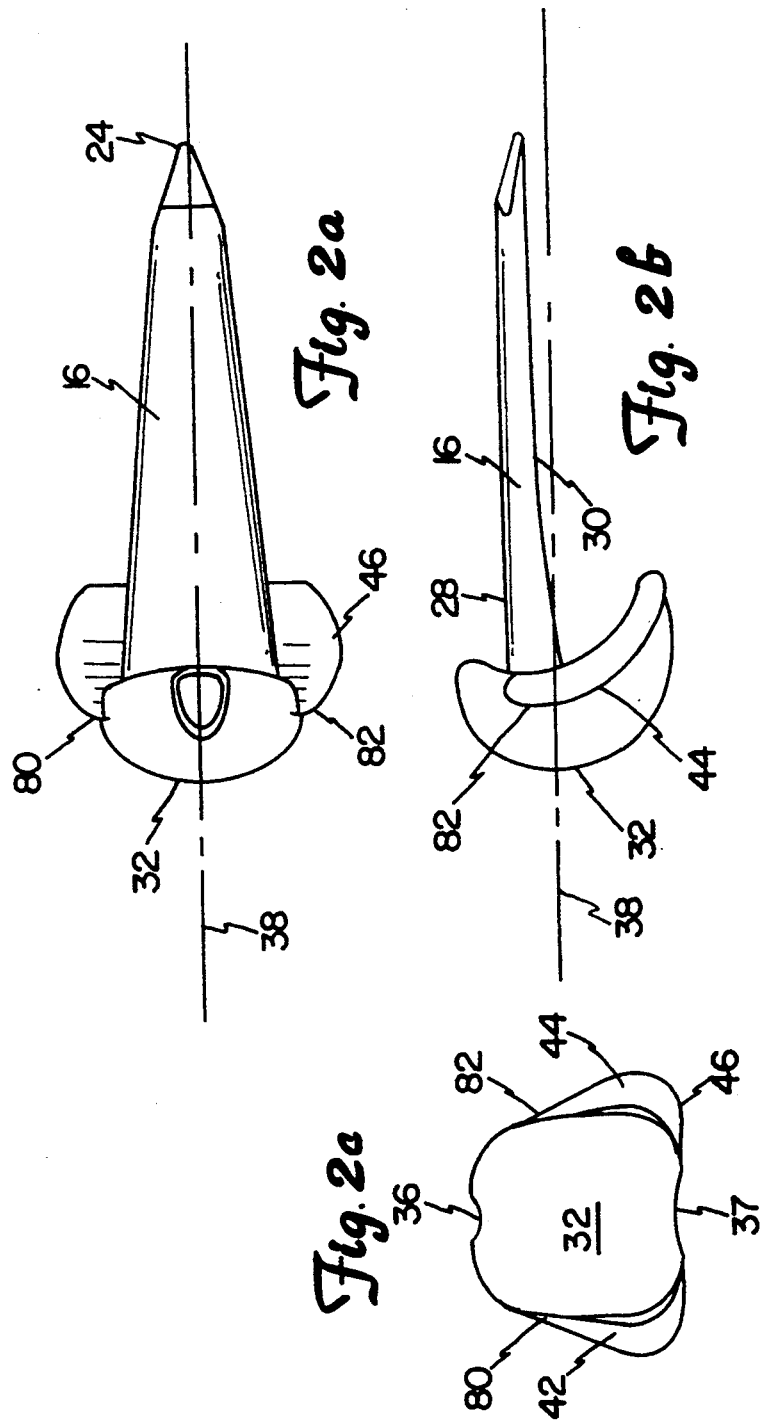

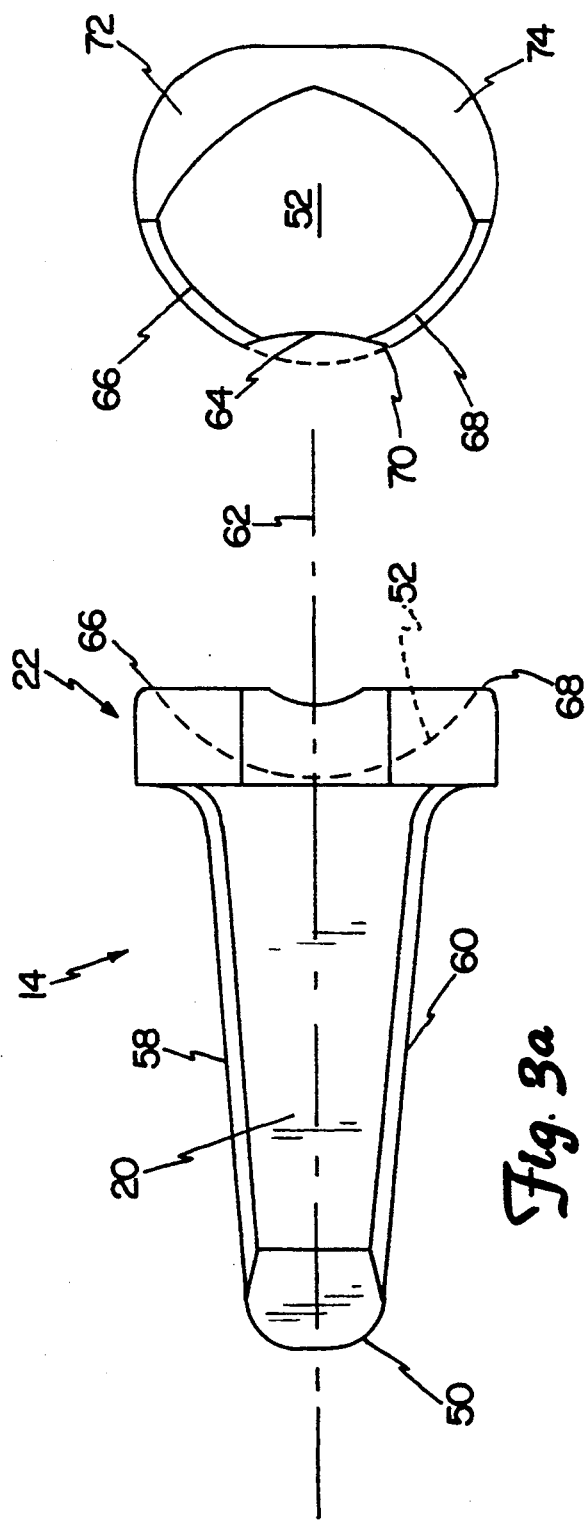
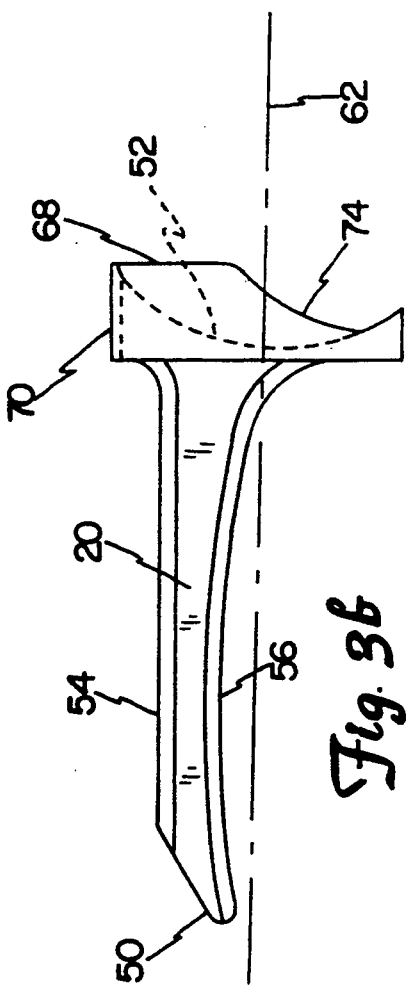
Fig. 3a
Fig. 3b

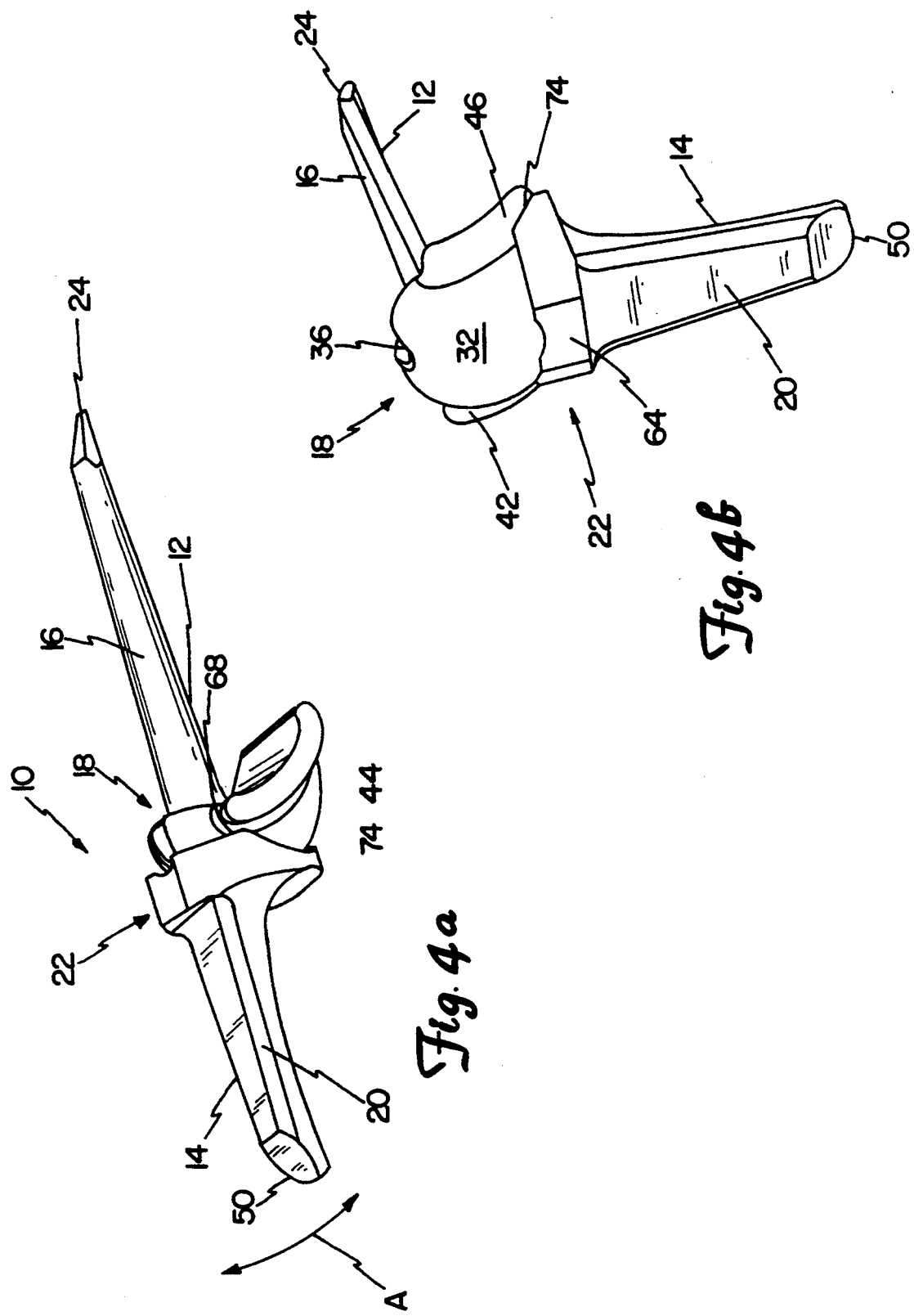

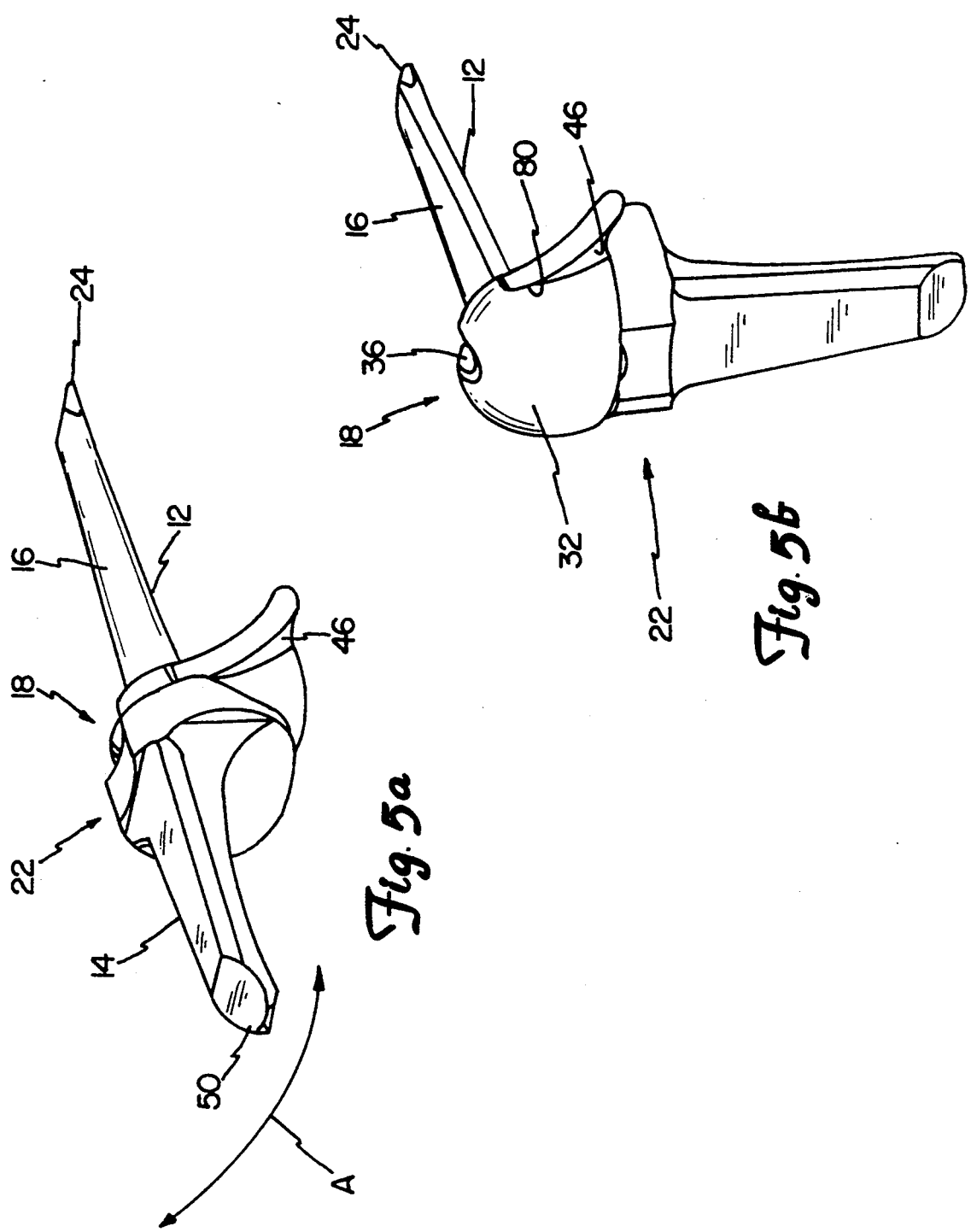

PROSTHESIS FOR REPLACEMENT OF JOINTS BETWEEN LONG BONES IN THE HAND

BACKGROUND OF THE INVENTION

This invention relates to joint prostheses particularly adapted for replacing a joint between two of the long bones of the hand such as the joint between the metacarpal and the first phalanx that articulates with the metacarpal.

The joints between elongated bones of the hand can be damaged by accident or by diseases such as rheumatoid arthritis and osteoarthritis and often need to be surgically replaced. Procedures for replacing damaged or diseased joints often have involved surgical removal of substantial portions of the bone adjacent a joint's articulating surfaces and implantation of an articulating prosthesis. The surgical procedure often involved removing not only substantial portions of bone but also of soft tissue attachments between the bony ends of the joint. This, in turn, has often required that the articulating ends of the prosthesis be fastened together in such a manner that they are not readily separated. Pivoting of the joint in the lateral (that is, in the radial/ulnar direction) was permitted in some prosthesis variations and not permitted in others, the degree of pivoting generally being independent of the degree of flexure of the fingers. A finger joint of this general type is shown in Lewis, U.S. Pat. No. 4,231,121 issued Nov. 4, 1980, which shows a prosthesis having a spherical bearing surface that articulates in a spherical recess.

Certain finger joint prostheses have been provided in which the prostheses were provided with stems having articulating, opposed heads and in which the heads were permitted limited lateral pivoting movement with respect to one another. One such prosthesis is shown in White, U.S. Pat. No. 4,242,759, issued Jan. 6, 1981. The articulating heads described in the White patent contained mating ridges and troughs, the contact between the ridges and troughs varying as the joint was flexed.

It is desired to provide a prosthesis so configured and arranged that its surgical implantation does not involve substantial disruption of soft tissue connections between the articulating bones nor removal of substantial portions of the bones themselves. Desirably, such prostheses duplicate closely the articulation afforded by a natural joint.

SUMMARY OF THE INVENTION

A joint prosthesis is provided which can readily be implanted without substantial removal of bone nor disruption of soft tissue connections between the bones. Mimicking the movement of normal physiological joints, the prostheses of the invention permit limited lateral pivoting of one bone with respect to the other when the bones are substantially aligned (that is, when the fingers are extended) but restrain such lateral movement when the bones are flexed through a predetermined angle.

The prosthesis includes a first member having an elongated stem for reception in one of the elongated banes, and a head remote from the stem. The head is provided with a convex articulating surface and also lateral articulating surfaces positioned on each side of the convex surface. A second member of the prosthesis has a stem for reception in the other of the two elongated bones, and includes a base remote from the stem. The base of the second member has a concave articulating surface and also lateral articulating surfaces on each side of the concave articulating surface. The concave and lateral articulating surfaces of the second member are adapted to engage and articulate with the respective convex and lateral articulating surfaces of the first member. The concave and convex surfaces enable articulation of the joint both in extension/flexion and in the radial/ulnar direction. Of importance, the lateral articulating surfaces of the first and second members are positioned to fully engage and articulate with each other to restrain lateral articulation only when the bones are articulated through a predetermined minimum degree of flexion, preferably at least 30°. Moreover, the articulating surfaces are so positioned that at 90° of flexion, the force between the members is borne primarily by the lateral articulating surfaces rather than by the convex and concave surfaces. In this manner, the phalanx is permitted a range of radial/ulnar (referred to sometimes herein as "lateral") articulation when the phalanx is extended, but is restrained from substantially all lateral movement when the joint is flexed through 90°. Preferably, the lateral articulating surfaces are so positioned as to contact one another when the fingers are extended only as the phalanges undergo a predetermined degree of lateral pivoting with respect to the metacarpals, the amount of such pivoting decreasing as the fingers are flexed through a predetermined are, such as from 60° to 90°, such that substantially no pivoting movement is permitted when flexure has reached the end of that arc.

Prostheses of the invention may be provided in kit form that includes several first members and several second members, the first members varying from one another by virtue of the orientation of their stems, the lateral angle between the stem axes of one prosthesis varying by at least 5° from the lateral angle between the stem axes of another prosthesis in the kit. Particularly, the stems of the first and second members have longitudinal axes that lie in planes that are generally parallel to the dorsal surfaces of the bones in which they are received. However, the axes of the first and second members may not be aligned or parallel, but may deviate from parallelism through up to about 15° in the dorsal plane to more closely match the angle between different ones of the elongated bones of the hand.

The head of the first member and the base of the second member are sufficiently narrow, measured in the radial/ulnar direction, as to avoid interference with the collateral ligaments of the joint, thereby enabling these ligaments to be preserved.

DESCRIPTION OF THE DRAWINGS

FIGS. 1A, 1B and 1C are dorsal, lateral and distal end views of a first member of a prosthesis of the invention;

FIGS. 2A, 2B and 2C are dorsal, lateral and distal end views of a modified version of a first member of a prosthesis of the invention;

FIGS. 3A, 3B and 3B are dorsal, lateral and proximal end views of a second member of the prosthesis of the invention;

FIGS. 4A and 4B are perspective views showing different degrees of articulation of a prosthesis of the invention employing the first member of FIGS. 1A, 1B and 1C;

FIGS. 5A and 5B are perspective views showing different degrees of articulation of a prosthesis of the invention employing the member shown in FIGS. 2A, 2B and 2C.

DESCRIPTION OF THE PREFERRED EMBODIMENT

Figure 6:
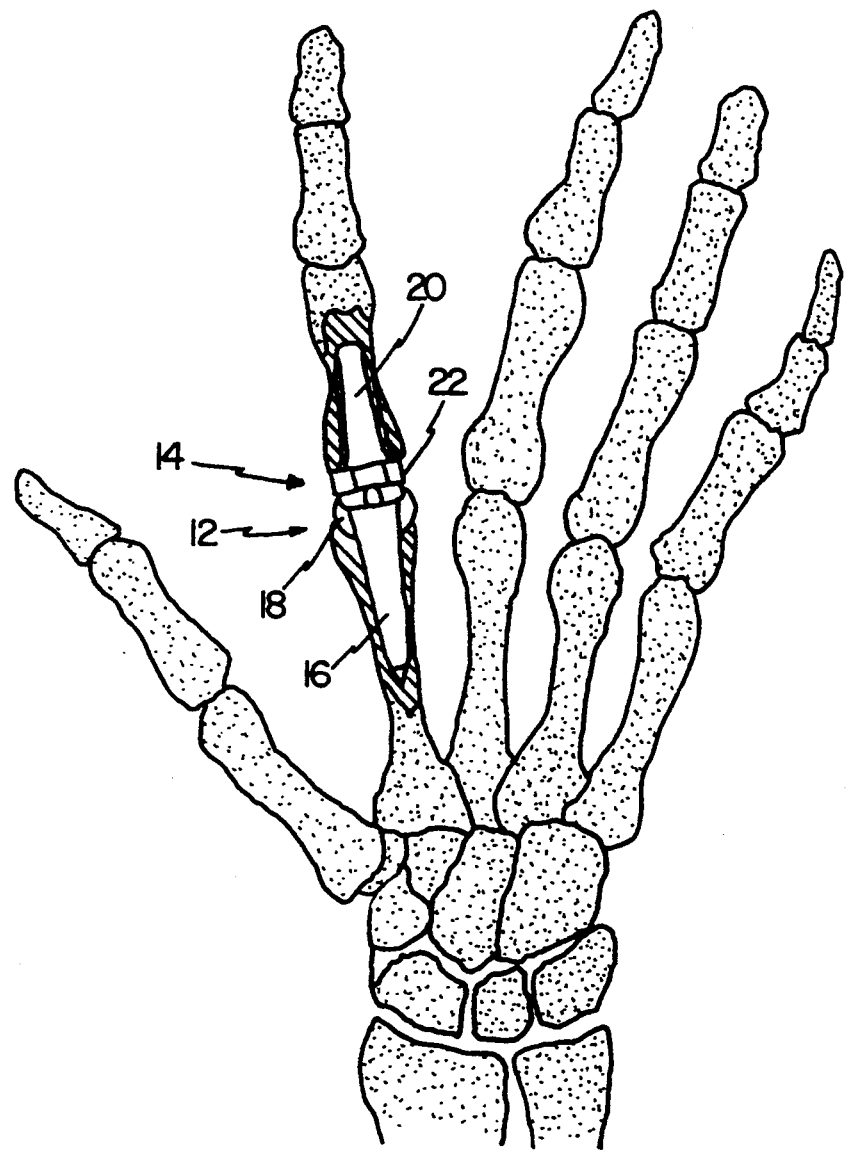
FIG. 6 is a dorsal view of the bones of the hand with a prosthesis of the invention as implanted.

For ease of understanding, the invention is described below with reference to the metacarpal/phalanx joint.

Referring first to FIGS. 4A, 4B and 6, a prosthesis of the invention is shown at 10 as comprising a first member 12 and a second member 14. Member 12 includes a stem 16 for reception in the marrow cavity at the distal end of a metacarpal, and has an articulating convex head designated generally as 18. Member 14 includes a stem 20 for reception in the marrow cavity at the proximal end of a phalanx, and includes a concave base portion shown generally at 22 that is curved to articulate with the head portion 18 of the first member.

Member 12 shown in FIGS. 4A and 4B is depicted in greater detail in FIGS. 1A, 1B and 1C. Stem 16 has a longitudinal axis "R", has a sharpened proximal end 24, and desirably, is generally triangular in cross section as shown at 26 in FIG. 1C. The stem has dorsal and volar surfaces 28, 30 (FIG. 1B), and extends generally in a plane parallel to the dorsal surface of the bone (not shown) of the metacarpal into which is to be inserted.

At its distal end, the stem 16 is provided with an enlarged head 18 having a generally spheroidal distally facing surface 32. Surface 32 extends toward the palmar direction and then more sharply proximally as shown at 34 in FIG. 1B. The palmar and dorsal facing portions of the surface 32 are provided with elongated grooves 36, 37 to aid in proper orientation of the member 12 during implantation and also to receive the extensor and flexor mechanism soft tissues.

Spherical surface 32 is formed about an axis 38 as shown in FIGS. 1A and 1B, and it will be noted from FIG. 1B that the stem 16 is spaced dorsally from the axis 38 so as to more closely approach the normal anatomy of the distal end of the metacarpal. If desired, the head 18 may be formed as a generally hemispherical shell having a recessed, inner surface 40 (FIG. 1B) to which the proximal end of the stem 16 is attached, as by welding or, more preferably, by being machined from a single blank of material. The distal end of the metacarpal may be surgically sculpted so as to be received within the recessed head 18, thereby reducing the amount of bone that must be removed. If desired, the head may be made solid, that is, not be recessed, for the purpose of reducing difficulty of machining the head shape.

Extending laterally (that is, in the radial/ulnar direction) from the side of the spheroidal surface 32, and spaced proximally from the distal end of that surface, are lateral articulating surfaces 42, 44. Note, from FIG. 1B, that the spheroidal convex articulating surface 32 may be formed about a point "P", and the lateral articulating surfaces (represented by surface 44 in FIG. 1B) curve in the volar direction and then proximally from the spheroidal surface and may be formed about a lateral axis (such as axis "A" in FIG. 1B) spaced proximally from said point P. These surfaces, as shown best in FIG. 1B, are distally facing near the axis 38 and then curve volarly and proximally (in the direction of the stem) as shown at 46 in FIG. 1B. Note that the surface 46 merges proximally into the surface 34.

FIGS. 3A, 3B and 3C depict the second member 14 of the prosthesis, this member having a base 22 and a stem 20. Stem 20 is generally oblong in cross section, tapering distally to a sharpened end 50 receivable in the marrow canal at the proximal end of a proximal or first phalanx. The stem terminates distally (with respect to the anatomy of the hand) in the base 22, the latter having a concave, desirably generally spheroidal and proximally facing articulating surface 52. Stem 50 has generally broad, flat dorsal and volar sides 54, 56 and narrower, distally converging lateral sides 58, 60. Viewed from the dorsal side as in FIG. 3A, the stem and typically the base 22 are symmetrical with respect to the axis 62 of the spheroidal, proximally facing articulating surface 52. As shown in FIG. 3B, however, the stem 20 is offset dorsally from the axis 62 so as to better conform to the anatomy of the proximal end of the proximal (first) phalanx.

The base 22 of the second member 14 includes a longitudinally extending groove 64 to aid in proper orientation of the member 14 during implantation and also to receive the extensor mechanism soft tissues. The proximally facing surface of the base 22 extending around about the spheroidal recess 52 includes proximally facing, generally planar surfaces 66, 68 about the periphery of the base near the, dorsal-facing edge 70 of the base, and curved portions extending dorsally and distally as shown at 72 and 74 in FIG. 3C.

Referring now to FIG. 4A, the concave, preferably spheroidal surface 52 of the base 22 of second member 14 is shaped to receive in articulating contact the convex, desirably spheroidal distally facing surface 32 of the head 18 when the members 12 and 14 are suitably implanted in the confronting ends of the metacarpal and proximal (first) phalanx bones of the hand. The distally facing portions of the lateral surfaces 42, 44 closely confront but are slightly spaced from the proximally facing surfaces 66, 68 of the base 22 of the second member so that when the stems 16, 20 of these members are generally aligned (as when the fingers are extended), some lateral pivoting movement of the phalanx is permitted as shown by arrow A in FIG. 4A. Contact between the surfaces 68, 44 and 66, 42, respectively, limit the amount of radial/ulnar lateral movement afforded the stem 20 when the fingers are extended.

As the finger is flexed from the position shown at zero degrees flexion in FIG. 4A to the position at 90 degrees flexion shown in FIG. 4B, the respective curved surfaces 72, 74 of the second member approach and contact the curved volarly and proximally extending portions 46 of the lateral articulating surfaces 42, 44 of the first member. When flexion of the finger has reached 90 degrees, the primary load between the two members is borne by the lateral articulating surfaces 42, 44 of the first member, and as such, radial/ulnar lateral pivoting of the second member 14 with respect to the first member is substantially and desirably completely restrained.

Referring again to FIG. 1A, it will be noted that the stem 16 extends proximally in the dorsal plane at an angle B from the axis 38. Desirably, the prosthesis of the invention is provided in a kit form that includes at least prostheses specifically designed for fitting different ones of the metacarpal/phalanx joints. The angle B, for example, can range up to 15° on either side of the axis 38, the angle being measured in a plane parallel to the dorsal surface 28. The purpose of the offset indicated by the arrow B in FIG. 1A is to more accurately position the head 18 of the first member with respect to the axis of the metacarpal within which the stem 16 is received. It is here noted that the second, third, fourth and fifth metacarpals vary in angulation of the articulating head to the long axis of the metacarpal bone in the coronal plane of the arm. Depending on the metacarpal chosen, as much as a fifteen degree angle is prevalent.

The embodiment shown in FIGS. 2A, 2B and 2C is identical to that shown in FIGS. 1A, 1B and 1C except for two features, and similar elements are given the same identifying numerals. First, it will be noted that the stem 16 when viewed dorsally as in FIG. 2A does not deviate in the dorsal plane from the axis 38. As taught above, the first member typified in FIGS. 2A, 2B and 2C may appropriately be implanted in the middle or ring finger metacarpal. Second, it will be noted that the lateral articulating surfaces 42, 44 are of full width laterally of the portion 46 of the surface that extends generally volarly and proximally in the direction of the stem. However, near the axis 38 of the member, the lateral articulating surfaces become substantially narrower in the dorsal direction, as shown at 80, 82 in FIG. 2C.

The purpose of narrowing the lateral articulating surfaces in this manner is to enable greater radial/ulnar swinging movement of the phalanges when the fingers are extended, and this feature is shown particularly in FIG. 5A by arrow A. Here, the second member 14 may be swung laterally through a greater arc when the fingers are extended. However, as the joint is pivoted through 90 degrees, as shown in FIG. 5B, the curved surfaces 72, 74 of the second member come into contact to an increasing extent with the lateral articulating surfaces of the first member such that at 90 degrees, the force between the articulating members is borne primarily by the lateral articulating surfaces.

The first and second members of the prosthesis of the invention may be manufactured from any of the materials that have been found acceptable for use in articulating joint prostheses, including, for example, ultra high molecular weight polyethylene, stainless steel, and various metal alloys. The first member, for example, can be made from metal material and the second from ultra high molecular weight polyethylene. For strength, it is desired that the members of the prostheses be integrally formed, as by machining, from solid blanks of material rather than being formed by joining together preformed portions of such members.

For implantation, a straightforward surgical procedure is employed. Access to the metacarpal/phalanx joint is performed dorsally. The bony joint segments are exposed, care being taken to preserve as much as possible soft tissue connections. The opposing bone ends are surgically sculpted to receive the head 18 and base 22 of the first and second members, respectively, care being taken again to avoid damage to soft tissue connections. Surgical access also is gained to the marrow cavities of the respective bones, and the stems are then implanted in the marrow cavities using bone cement in the usual fashion. It is contemplated that it may be appropriate in some circumstances to cause the stems of the prosthesis members to fit fairly tightly in the marrow cavities of the bones in which they are implanted, omitting the need for bone cement. In this event, the surfaces of the stems desirably are shaped or treated to encourage bone ongrowth or ingrowth, as by providing the stems with porous surfaces, by applying to the stems a cell adhesion promoter such as collagen or the like, etc.

While a preferred embodiment of the present invention has been described, it should be understood that various changes, adaptations and modifications may be made therein without departing from the spirit of the invention and the scope of the appended claims.

What is claimed is:

1. A joint prosthesis for replacing a joint between two articulating elongated bones of a hand, comprising
   a first member having an elongated stem for reception in one of the elongated bones, and a head remote from the stem, the head having a spheroidal convex articulating surface and lateral articulating surfaces adjacent the convex surface and on each side thereof; and
   a second member having a stem for reception in the other of the two articulating bones, and a base remote from the stem, the base having a spheroidal concave articulating surface and lateral articulating surfaces on each side thereof, the concave and lateral surfaces being adapted to engage and articulate with the respective convex and lateral articulating surfaces of the first member;
   the lateral articulating surfaces of the first and second members being positioned to fully engage and articulate with each other to thereby restrain lateral articulation only when the bones are articulated beyond at least 30 degrees of flexion and wherein at 90 degrees of flexion, force between said members is borne primarily by said lateral articulating surfaces.

2. The joint prosthesis of claim 1 wherein said lateral articulating surfaces are positioned to limit lateral articulation between the bones when the bones are longitudinally aligned.

3. The joint prosthesis of claim 1 wherein said lateral articulating surfaces are positioned so as not to restrict lateral articulation between the bones when the bones are longitudinally aligned.

4. The joint prosthesis of claim 3 wherein said lateral articulating surfaces are positioned and have a length so as to come into articulating contact and gradually reduce a degree of permitted lateral articulation of the bones as the latter are flexed through a predetermined arc of flexion.

5. The joint prosthesis of claim 4 wherein said predetermined arc of flexion ranges from about 60° to about 90° degrees of flexion.

6. The joint prosthesis of claim 1 wherein said spheroidal convex articulating surface of the first member is formed about a first axis and wherein the stem of the first member has a longitudinal axis lying in planes generally parallel to the dorsal surfaces of the bones in which they are to be received, said stems being positioned such that when said planes are general parallel and said convex and concave surfaces are engaged, the stem axes lie] at a predetermined lateral angle to said first axis.

7. The joint prosthesis of claim 6 wherein said lateral angle ranges from about −15° to about +15° degrees.

8. A kit for use in surgical replacement of one or more joints between elongated bones of the hand, comprising a plurality of the prostheses of claim 6 wherein said lateral angle varies from one such prosthesis to another within said kit by at least 5°.

9. The joint prosthesis of claim 1 wherein said spheroidal convex articulating surface is formed about an axis parallel to but spaced in the volar direction from the axis of the stem.

10. The joint prosthesis of claim 1 wherein the lateral articulating surfaces of the first member extend laterally outwardly from said spheroidal convex articulating surface and are formed on a radius about a laterally extending axis.

11. The joint prosthesis of claim 10 wherein said spheroidal convex articulating surface is formed at a predetermined radius from a point, and wherein said lateral articulating surfaces have curved articulating surfaces curving in the volar direction and then proximally away from the spheroidal surface and which are formed about an axis spaced proximally from said point.

12. A joint prosthesis for replacing a joint between two articulating elongated bones of a hand, comprising
   a first member having an elongated stem for reception in one of the elongated bones, and a head remote from the stem, the head having a spheroidal convex articulating surface and lateral articulating surfaces adjacent the convex surface and on each side thereof; and
   a second member having a stem for reception in the other of the two articulating bones, and a base remote from the stem, the base having a spheroidal concave articulating surface and lateral articulating surfaces on each side thereof, the concave and lateral surfaces being adapted to engage and articulate with the respective convex and lateral articulating surfaces of the first member;
   the lateral articulating surfaces of the first and second members being positioned so as to come into articulating contact and to gradually engage and articulate with each other to thereby restrain lateral articulation as the elongated bones are flexed and wherein at 90 degrees of flexion, force between said members is borne primarily by said lateral articulating surfaces.

13. The joint prosthesis of claim 12 wherein said spheroidal convex articulating surface of the first member is formed about a first axis and wherein the stem of the first member has a longitudinal axis at a predetermined lateral angle to said first axis.

14. A kit for use in surgical replacement of one or more joints between elongated bones of the hand, comprising a plurality of the prostheses of claim 13 wherein different ones of said prostheses have different predetermined lateral angles.

* * * * *